United States Patent [19]

Block, Jr.

[11] Patent Number: 5,394,881
[45] Date of Patent: Mar. 7, 1995

[54] LIQUID INGRESS CONTROL FOR A GAS MONITOR

[75] Inventor: Frank E. Block, Jr., Columbus, Ohio

[73] Assignee: Instrumentarium Corp., Helsinki, Finland

[21] Appl. No.: 59,944

[22] Filed: May 7, 1993

[51] Int. Cl.$^6$ .............................................. A61B 5/08
[52] U.S. Cl. ............................. 128/716; 128/205.12; 128/205.27
[58] Field of Search ............... 128/716, 719, 730, 760, 128/205.12, 205.27; 73/16, 23.3; 340/620, 618; 422/84

[56] References Cited

U.S. PATENT DOCUMENTS 4,197,858  4/1980  Osborn ........................... 128/205.12
4,799,374  1/1989  Bossart et al. ................... 128/205.12

Primary Examiner—Lee S. Cohen
Assistant Examiner—Bruce M. Green
Attorney, Agent, or Firm—Mueller and Smith

[57] ABSTRACT

Liquid incursion into the gas analyzer or monitoring components of a gas analyzer of a variety employed in medical practice is prevented by a sequence of components performing under computer control. A liquid detector is positioned immediately downstream of the liquid separator/trap of the apparatus to detect any failure of that separating system. Should an incursion occur, the output of the detector will cause a safety valve to block further passage of materials into the monitoring components. The removable separator/trap components are monitored by interlock sensors. Upon appropriate signaling of such removal, a purging valve is actuated to employ atmospheric air made available by the removal of the separator/trap unit to purge the encroaching liquid from the forward components of the analyzer assembly.

23 Claims, 4 Drawing Sheets

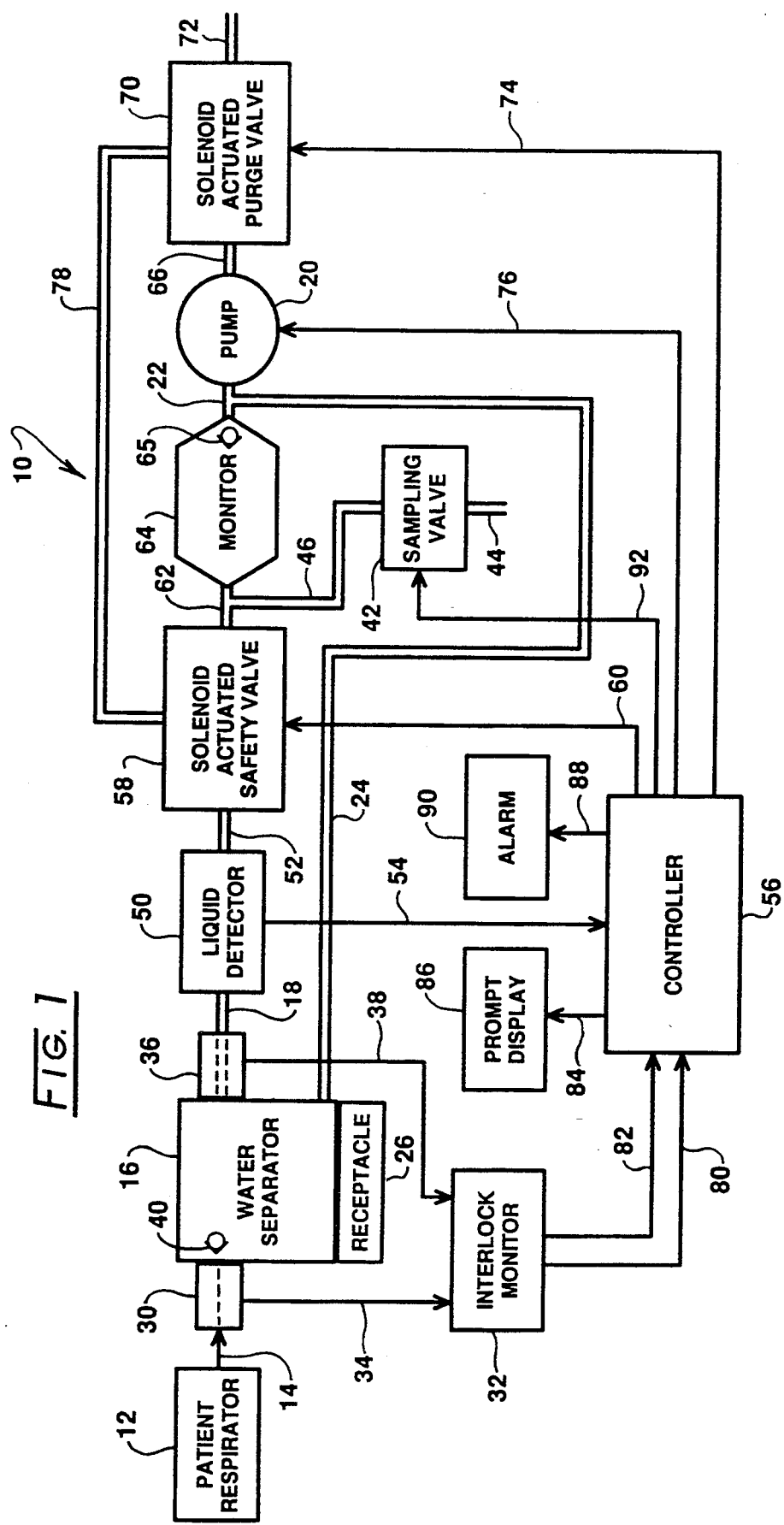

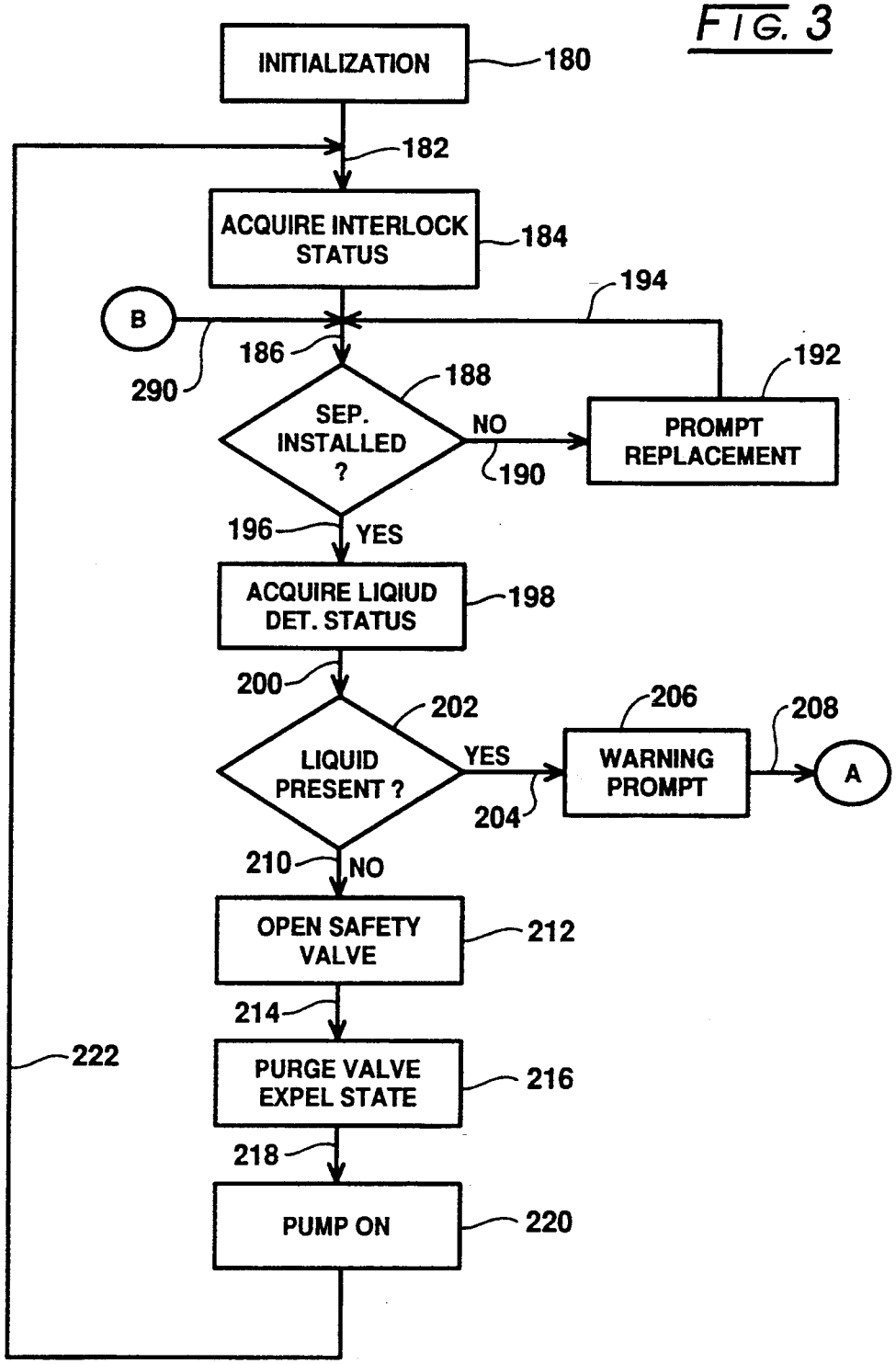

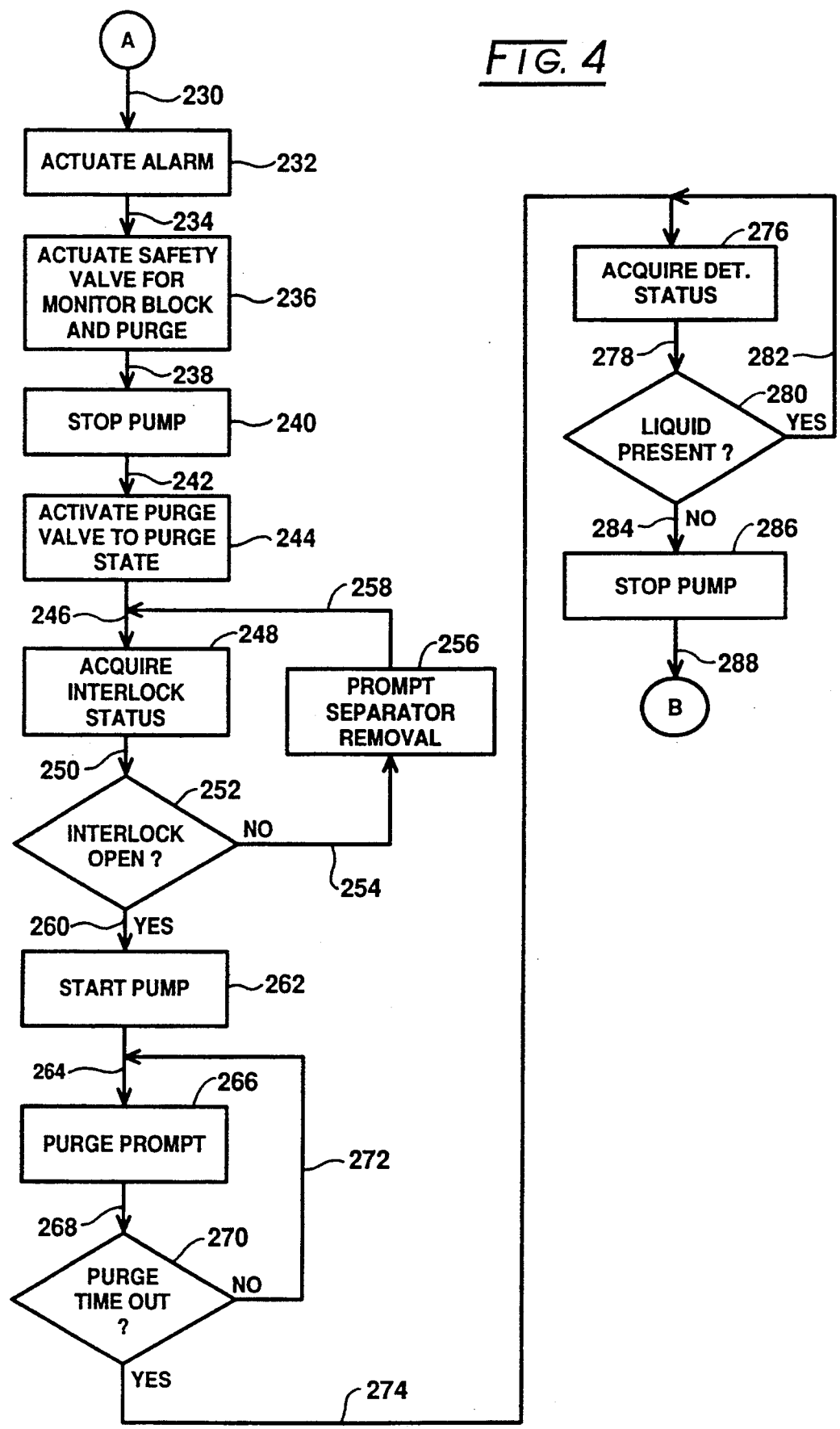

LIQUID INGRESS CONTROL FOR A GAS MONITOR

BACKGROUND OF THE INVENTION

Gas monitors are used in medical care situations to determine the content of a patient's inspired and/or expired gas. Situations in which a gas monitor are used include: during the administration of general anesthesia; during the administration of regional anesthesia; in the intensive care unit; in the recovery room; and other various situations.

Generally, there are two types of gas monitors, mainstream monitors and sidestream monitors. A mainstream monitor analyzes gas at or near a patient's airway and is usually only used to measure $CO_2$. The side-stream monitor, which is the most common form of gas analyzing system, utilizes a pump mechanism to sample gas from a patient's airway and transport the gas to a gas analyzer located at an area which will be from about a few to 100 feet away.

Gas analyzers use different methods to detect different gases. Infrared light may be used to detect any substance that absorbs infrared light. The most typical gases an infrared detector is designed to detect are: $CO_2$, $N_2O$ and various anesthetic agents. Paramagnetic detectors may be used to detect any substance that will shield or attenuate a magnetic field. Paramagnetic detectors are most commonly used to detect $O_2$. Other analysis techniques include mass spectrometry and Raman scattering. Mass spectrometry identifies the chemical components of a substance with the use of a mass spectrometer. A mass spectrometer, which is most commonly used to determine the proportion of $N_2$ in a sample, passes streams of ions through electric and magnetic fields which separate ions of different masses. Raman scattering utilizes laser light, which loses energy as it encounters and scatters off of a molecule, to identify substances.

Any liquid, upon entering a gas analyzer may temporarily, or in some cases, permanently damage its detection mechanism which usually is located in an analysis chamber. For example, liquid entering an infrared analysis chamber will absorb a great deal of infrared light and cause a false gas content reading. Moreover, the analysis chamber will require cleaning or must be replaced if liquid coats the analysis device.

Side-stream gas monitors, which transport a patient's exhalation to a remote area to be analyzed, tend to collect liquid within them. A human exhalation contains moisture in the form of mucous, saliva, and in certain patient conditions, blood. Moreover, in some situations, a patient may be fed air from a heated humidifier at close to 100% relative humidity and at body temperature. As the side-stream monitor extracts sample gas from the patient the gas travels through the sample tubing toward the gas monitor. While the gas travels toward the gas monitor it cools to room temperature and liquid condenses inside the tubing. This condensed liquid, accompanied by the patient's additional secretions of blood and mucus, is swept by the pump toward the gas analyzer. If the liquid is not stopped it will enter the analysis chamber and cause severe problems.

To ensure that liquid does not reach the gas analyzing stage of a gas monitor, a number of solutions have been attempted. Nation tubing, which is a semi-permeable tubing, may be placed in the gas monitor to prevent liquid from entering the analyzer. (Nafion is a trademark of E. I. dupont de Nemours Co.) This is a special type of tubing which is permeable to water yet not permeable to gas. Thus, as water condenses in the sample and travels into a section of Nation tubing it will pass through the tubing walls to the atmospheric environment while the now separated gas remains in the tubing and continues toward an analysis position. A water filter placed before the gas analyzer may also be used to stop liquid from reaching it. Such devices filter liquid and secretions from a patient's exhalations, however, they tend to be unreliable. The most common, and effective method of ensuring that liquid does not reach a gas analyzer is through the use of a water trap. Water traps are devices which are geometrically designed such that liquid contained in a gas sample drips into a water receiver. Early water traps utilized a Y-shaped member directed into a water receiver to force condensed water droplets to "fall" into the receiver while pure gas passed over and through a branching conduit out of the receiver. More recent designs for water traps incorporate a gas permeable membrane as a filter to assist with and assure proper water separation. For example, U.S. Pat. No. 4,886,528, entitled "Tubular Water Separator for a Gas Analyzer", by Aaltonen, et al., describes a water receiver arrangement for a gas analyzer which collects liquid that has been separated from sample gas in combination with a gas permeable membrane which assists in separating liquid from the gas sample and ensures that liquid does not travel past the trap toward the gas analyzer.

Water traps are not always effective in separating liquid from the sample gas to avoid harm to the gas analyzer. There is a possibility that a water trap without an effective gas permeable membrane will allow liquid and secretions to pass, and thus enter and damage a downstream analysis chamber. Gas permeable membranes must be periodically replaced. After a period of use dependent on the amount of secretions which have been separated from the sample gas, the membrane will become occluded such that gas is no longer able to pass. When this occurs the water trap assemblage should be discarded and replaced. To avoid the cost of such replacement, technicians sometimes attempt to clean the assemblage by forcing air at high pressure through it. This procedure may cause the membrane to rupture, thus allowing liquid and secretions from subsequent use to pass through the trap unobstructed, resulting in temporary or permanent damage to the gas analyzer.

To avoid damage to gas analyzers, a technique called "reverse flushing" has been attempted. With this "reverse flushing" technique, upon a determination that liquid has passed the liquid separation point, (the water trap) gas flow of the analyzer pump is reversed and the resultant purging gas drives liquid and secretions out of the gas analyzer, conducting back toward the patient. The "reverse flushing" technique has been abandoned by practitioners because of a danger of instrument contamination, it being impossible to disinfect the internal components of a gas monitor. Thus when "reverse flushing" occurs the patient who would encounter the gas and effluvia blown away from the gas analyzer is subject to cross contamination from residue of previous patients.

Significant improvements in the application and use of gas monitors in conjunction with water traps may be realized if liquid or other debris, once past the water trap, could be detected and safely purged from the gas monitor without the risk of cross-contamination, before reaching the gas analysis chamber within a gas monitor.

SUMMARY

The present invention is addressed to an improved gas analyzer, particularly as employed in the medical field in conjunction with respiratory support systems. Liquids and similar contaminants which are not entrapped or separated by the separator system of the analyzer assembly are detected by a liquid detector strategically positioned at the outflow of the separator component. Upon such detection of liquid or related effluvia, damage to downstream gas analyzing components is prevented by blockage of the fluid passageways leading to them. This is carried out, for example, under microprocessor control utilizing a solenoid actuated valve. Corrective action conventionally requires the intervention of an operator for the purpose of removing the separator/trap housing. To assure that this has been carried out, a separator interlock monitor is provided which generates a disconnect signal upon separator removal.

When the separator is so removed, opportunity is present for purging the forward passageways of the apparatus using its gas pump in conjunction with a purge valve and atmospheric air. This latter, atmospheric air is made available because of the separator removal previously carded out or through the utilization of a valved atmospheric air input normally employed as an input for simple room air as a reference gas. Thus, controlled and safe purging may take place within the apparatus without the possibility of patient cross-contamination. Restarting of the analyzer apparatus in a normal operational mode occurs only upon the removal of the incursion output condition of the liquid detector.

Other objects of the invention will, in part, be obvious and will, in part, appear hereinafter.

The invention, accordingly, comprises the apparatus and system possessing the construction, combination of elements, and arrangement of pans which are exemplified in the following detailed disclosure. For a fuller understanding of the nature and objects of the invention, reference should be had to the following detailed description taken in connection with the accompanying drawings.

BRIEF DESCRIPTION OF THE DRAWINGS

FIG. 1 is a block schematic diagram of a gas separator assembly incorporating the features of the invention;

FIG. 3 is a flow chart of a general control program employed with the apparatus of the invention; and FIG. 4 is a flow chart of a fluid incursion response program employed with the program of FIG. 3.

DETAILED DESCRIPTION OF THE INVENTION

Figure 2A:
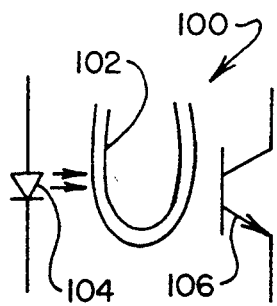
FIG. 2A is a schematic diagram of a liquid detector of a light occlusion variety.

In the discourse to follow, the improved gas analyzer assembly of the invention is described in conjunction with a representation of a gas analyzer product sold under the trade designation "Capnomac" by Datex Instrumentarium Corp. of Helsinki, Finland. Salient features of that analyzer are described in U.S. Pat. No. 4,886,528 entitled "Tubular Water Separator for a Gas Analyzer" by Aaltonen, et al., issued Dec. 12, 1989, and assigned in common herewith which is expressly incorporated herein by reference.

Referring to FIG. 1, a gas analyzer assembly incorporating features of the invention is revealed in schematic form in general at 10. The assembly 10 functions, for example, in combination with a respirator system employed with patients in a hospital environment. That respirator system is represented in the figure in general at block 12. At least a portion of the liquid/gas flow in this system 12 is asserted at an input passage 14 of assembly 10. Because the fluid flow entering passage 14 will have a liquid content as well as various effluvia from time to time, those liquid-based contaminants are removed at a liquid or water separator component represented generally at 16. As described in the above-noted U.S. Pat. No. 4,886,528, the assembly 16 includes two chambers (not shown) which are separated by a gas permeable and water impermeable material or diaphragm. The gas component of fluid entering from passage 14 is drawn through this membrane or material into one of the noted chambers, thence into an intermediate passage represented schematically at 18 by a pump 20. The suction side of pump 20 is shown at conduit 22 which also is seen to communicate via a conduit or suction passage 24 back to the separator assembly 16. A smaller amount of vacuum or suction asserted from conduit 24 by the pump 20 is introduced to an oppositely disposed chamber formed in assembly 16 so as to promote the collection of liquid which fails to pass the noted diaphragm. This material is retained or collected within a removable receptacle represented at 26. In general, the separator component 16 is retained within a housing which is removably insertable or connectable within the apparatus 10 such that it may be withdrawn for the purpose of replacement. Additionally, the receptacle 26 requires emptying from time to time. It may be observed that upon removal of the housing retaining the water separator 16 components, passage 18 and suction conduit 24 will be open to the atmospheric environment. Gas analyzer systems may provide for other forms of liquid extraction, for example, filters or the like.

The interconnection of the separator input with input passage 14 is monitored by the sensor 30 of an interlock monitor system represented generally at block 32. A signal representing either the presence or absence of the assembly 16 in proper position is provided by the sensor 30 as represented by line 34 to the monitor 32. Correspondingly, the output flow of the water separator component is monitored by a sensor 36 of the interlock montor system 32 with respect to whether the output flow port thereof is in proper fluid flow communication with passage 18. The appropriate signal from sensor 36 as to that connection or disconnection is conveyed as represented by line 38. Sensing devices 30 and 36 may take any of a variety of configurations. For example, conventional microswitches may be employed to carry out their function. Also incorporated within the separator apparatus 16 is a check valve symbolically depicted at 40 which functions to block back flow into the input passage 14. The use of valve 40 in the instant system is optional, inasmuch as a purging cycle will be seen to be carded out only in the presence of an assured removal of pertinent water separator components.

Gas fluid having been treated by the water separator component 16 and flowing under the influence of pump 20 through the passage 18 is directed to a liquid detector 50 shown within the passage 18 which additionally is seen to extend from the detector at another component 52 of the intermediate passageway. Thus, the detector 50 input is at passage 18 and its output is at passage 52. Detector 50 functions to determine the presence of any liquid or effluvial contaminant at its input at passage 18 which may have passed through a defective water separator component 16. This may be occasioned by the failure of the noted diaphragm where that form of separator is in use or, for example, through a failure of personnel to empty the liquid recetpacle 26. In the event of the detection of such a liquid entering the detector 50 from passage 18, then an incursion output condition will ensue which is transmitted as represented at line 54 to a microprocessor driven controller represented at block 56. Controller 56 functions to immediately actuate a safety valve or flow control assembly represented at block 58 by communication therewith as represented at line 60. Safety valve 58 is seen to have a primary input at passage 52 representing the output of detector 50 and has a valve output as represented at passageway 62 which leads to the analyzer input of a gas analyzer or monitor represented at 64. The monitor 64 may be of any of a wide variety, for example, infrared based, paramagnetically based, or the like. Gas from its input 62 is drawn therethrough and past a safety check valve represented at 65 to the suction side of pump 20 as represented at passageway 22. The output side of pump 20 is shown leading to a passageway or conduit 66 which, in turn, is directed to the purge input of a solenoid actuated purge valve represented at block 70. An expel output of valve 70 is seen at passageway or conduit 72 leading to atmosphere and the valve 70 as well as the pump 20 are seen to be under the actuation control of controller 56 as represented by respective lines 74 and 76. Purge valve 70 also is configured having a purge output coupled with conduit or passageway 78 which is seen to lead to a third, purge inlet port of safety valve 58. Thus, valve 58 may be configured, as would valve 70, for example, as a three-way solenoid actuated valve. Where safety valve 58 is employed in a three-way fashion, when actuated by controller 56 to a blocking state, valve 58 will permit the passage of gas flow from passageway 78 to passageway 52. Alternately, the passageway 78 can be directly coupled to passageway 52.

Looking in more detail to the controller 56, it may be observed that the outputs of sensors 30 and 36, as submitted via respective lines 34 and 38 to interlock monitor function 32, are transmitted as connect outputs at respective lines 80 and 82 to controller 56 when the separator component housing at 16 is properly installed within the assembly 10. Where either of the sensors 30 or 36 detects an improper installation or no installation of the housing of separator component 16, then an appropriate disconnect output is transmitted via lines 82 and/or 80 to the controller 56. The controller 56 reacts to prompt the operator to install the separator component 16 through a display such as a liquid crystal display (LCD) as represented at lines 84 and block 86. Controller 56 additionally may generate an audible alarm to warn the operator of such a defect as represented at line 88 and block 90.

Similarly, where an incursion of liquid or effluvia or other improper non-gaseous material is detected at the liquid detector 50, an incursion output is provided at line 54 permitting the controller 56 to react by actuating the safety valve 58 from a flow state into a blocking state preventing the passage of gas and possible contaminants from passageway 52 into the valve. As before, an operator prompt may be provided at display 86 instructing as to the removal of the separator component 16, and/or emptying of the receptacle 26. At such time, the pump 20 may be actuated to an off state pending the carrying out of corrective procedures ultimately resulting in the clearing of liquid detector 50. As described hereinafter, such clearing may be carried out by requiring the removal of the housing of water separator component 16 such that a disconnect output is transmitted at lines 80 and 82 to the controller 56. This is then followed by the actuation of purge valve 70 and the re-starting of pump 20 to carry out a purging of the system in a reverse gas flow path towards the water separator component 16 by pumped air which may now be drawn from passageway or suction conduit 24 which is open to atmospheric air by virtue of the removal of the separator component 16 housing. Pumping continues, for example, for a predetermined time and at least until the incursion output condition at line 54 is no longer present. Purging air also may be accessed by actuating a sampling valve 42 to provide a pathway from conduit 44 through conduit 46 to passageway 62, thence through monitor 64 to conduit 22. Actuating control from controller 56 is represented by line 92. Reverse gas (air) flow also may be developed with appropriate pump selection by reversing the drive to pump 20. Sampling valve 42 normally provides for the circulation of atmospheric air through monitor 64 for the purpose of "zeroing" the latter devices.

The form of liquid detector 50 employed with the assembly 10 may assume any of a broad variety of topologies depending upon the type of liquid or effluvia anticipated to encroach into the passageway 18. Referring to FIG. 2A, a somewhat simple emitter-detector form of device is represented schematically and in general at 100. The approach represented at 100 utilizes, for example, a U-shaped transparent detector passage or tube 102 through which light from a light emitting diode 104 is directed to pass to be detected by a corresponding photodiode 106. Material within the tube 102 will tend to occlude light transmitted from the diode 104 to the detector 106 to provide an indication of a liquid incursion.

Figure 2B:
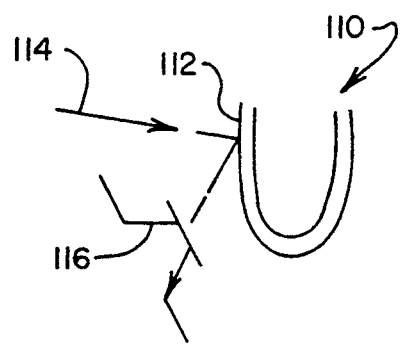
FIG. 2B is a schematic representation of a liquid detector utilzing laser scattering techniques.

Referring to FIG. 2B, a laser driven approach is represented generally and schematically at 110. Here, a detector passageway which is transparent as before is represented as curved tube 112 through which any such liquid would pass. The output beam of a laser as represented at arrow 114 is directed to one portion of tube 112 and any scatter from the tube may be detected by a photodetector represented at 116. With the approach shown, scatter is occasioned by the incursion of a liquid or other form of matter into the tube 112.

Figure 2C:
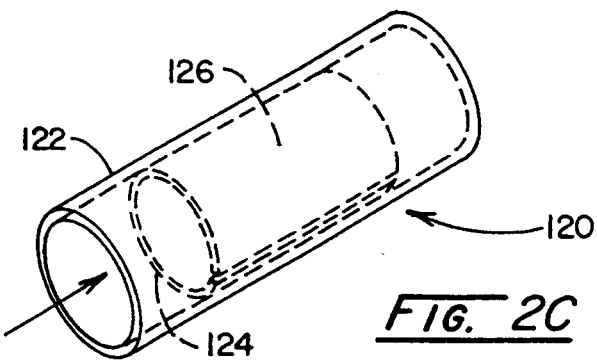
FIG. 2C is a schematic diagram of the passageway of a liquid detector incorporating capacitor plates.
Figure 2D:
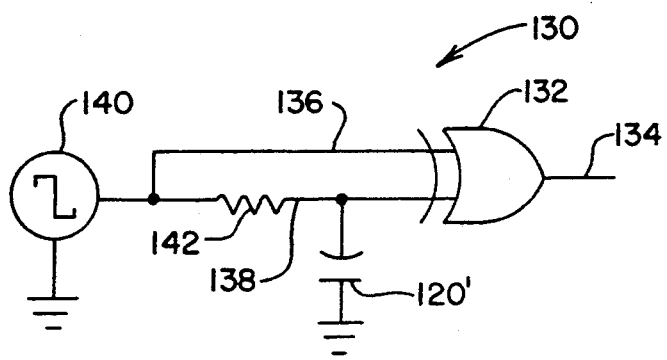
FIG. 2D is a schematic diagram of an exclusive OR logic circuit employed with the capacitor plates of FIG. 2C.

Looking to FIG. 2C, a capacitor based approach is represented generally at 120. With this approach, a tube coupled with passageway 18 as represented at 122 is formed having spaced-apart capacitor plates 124 and 126. A change in capacitance between these two plates 124 and 126 will occur with the incursion of a dielectric liquid. Looking additionally to FIG. 2D, a schematic representation of a circuit which may utilize the capacitor having plates 124 and 126 is represented in general at 130. Circuit 130 is predicated upon the logic associated with the utilization of an exclusive OR gate function as represented symbolically at 132. Exclusive OR logic will provide an output, for example, at line 134, when the inputs thereto at lines 136 and 138 are different or of different values. By connecting these inputs 136 and 138 with a relaxation oscillator 140 and providing an R-C circuit including resistor 142 and a capacitor identified at 120' in input 138, the output pulse resulting at line 134 will vary in width in dependence upon the capacitive value at capacitor 120'. This capacitor 120' is that seen in FIG. 2C at 120. Thus, as capacitance increases, the width of any given output pulse resulting from oscillator 140 will increase.

Figure 2E:
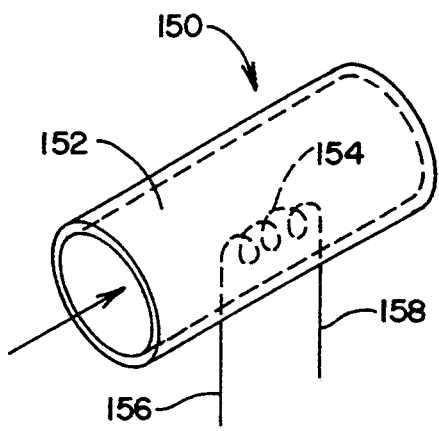
FIG. 2E is a schematic diagram of a temperature responsive resistor liquid detector technique.

Looking to FIG. 2E, a resistive approach to detection is represented schematically at 150. Here, a passageway extending through the detector 50 is represented at tube 152. Within tube 152 there is mounted a device which varies in resistance with temperature such as a platinum wire, thermister, or the like, which is represented at 154. As liquid encounters this device 154, its resistance will change to provide a varying voltage drop across its output at lines 156 and 158.

Figure 2F:
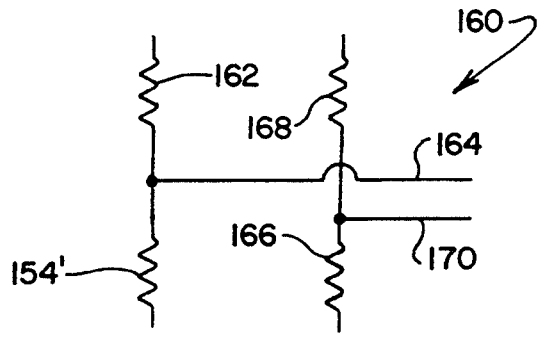
FIG. 2F is an electrical schematic diagram of a bridge circuit employing the sensing component described in connection with FIG. 2E.

Looking to FIG. 2F, a conventional bridge circuit which may be employed with the resistive approach 150 of FIG. 2E is represented in general at 160. Circuit 160 includes a resistor 154' which is equivalent to component 154 as described in FIG. 2E and is coupled with a complementing resistor 162, the mid point between these devices 154' and 162 being tapped by line 164. In similar fashion, a reference resistor is provided at 166 in conjunction with resistor 168, the mid point of which is tapped at line 170. Voltage differences thus developed between lines 164 and 170 may be employed for the purpose of liquid detection.

Other approaches will occur to those skilled in the art, for example, technology based upon electronic cell-counting instruments operating on the ion-conductivity principle may be employed. Such devices have been introduced to the field of technology by J. R. Coulter.

Referring to FIG. 3, a block diagrammatic representation of the general program under which the controller 56 may perform is presented. In the figure, as represented at block 180, the program commences with a conventional initialization procedure, following which as represented at line 182, the instructions presented at block 184 are carried out. Block 184 looks to the acquisition of the status of the interlock monitor 32 to determine whether the housing of the water separator component 16 is properly in place. The program then continues as represented at line 186 and block 188 to a determination as to whether the information thus acquired shows that the separator component 16 is properly installed. In the event that is not, then as represented at line 190, block 192, and line 194, the program dwells until proper installation is achieved. During this interval, as represented at block 192, the display 86 is activated to instruct the user to install the separator component 16. Where the information derived from lines 80 and 82 indicates that an interlock monitor connect output is present, then as represented at line 196 and block 198, the status of liquid detector 50 is acquired. The program then continues as represented at line 200 to block 202 where a determination is made as to whether an incursion output condition is at hand representing that liquid or some effluvia has passed the water separator assembly 16. In the event that it has, then as represented at line 204 and block 206, the controller 56 publishes a visual readable warning and the alarm 90 may be actuated at this point in time. The program then continues as represented at line 208 and node A.

Where no incursion output condition is at hand, then as represented at line 210 and block 212, the safety valve 58 is actuated to a flow state or open condition if it were not initially in that orientation. Then, as represented at line 214 and block 216, assurance is made that the purge valve 70 is actuated or is presently in an expel state providing for the passage of the gas from passageway 66 to passageway 72 and atmosphere. The program then continues as represented at line 218 and block 220 which provides for the actuation of pump 20 to an on condition. Then, as represented at loop line 222, the program returns to line 182.

Referring to FIG. 4, node A reappears in conjunction with line 230 extending to instructions at block 232. These instructions provide for the actuation of the alarm 90 so as to bring the liquid incursion to the attention of the operator. The program then continues as represented at line 234 and block 236 to provide for the actuation of the safety valve 58 for purposes of blocking passage of fluid into the monitor 64. This actuation of valve 58 into a blocking state then permits a subsequent purge operation as carded out in conjunction with purge valve 70. Then, as represented at line 238 and block 240, the pump 20 is stopped to hinder any further incursion of liquid and, as represented at line 242 and block 244, the purge valve 70 is actuated to assume a purge state forming a fluid flow path from passageway 66 at the suction side of pump 20 to the purge conduit 78. Thus, at this juncture, the liquid detector 50 has detected liquid; the safety valve 50 has been actuated to a blocking state; the pump 20 has been stopped; and the purge valve 70 now is prepared to purge the system. Next, as represented at line 246 and block 248, the status of the interlock monitor 32 is acquired and, as represented at line 250 and block 252, a determination is made as to whether the housing of separator apparatus 16 has been removed by the operator such that a disconnect output is present and responded to from lines 80 and 82 at the controller 56. In the event that is not the condition, then as represented at line 254 and block 256, the controller 56 actuates the prompt display 86 to instruct the operator to remove the separator. The program dwells at this position as represented at lines 258 and 246 until the interlock disconnect output is acquired. Upon the occasion of acquiring the disconnect status, then as represented at line 260 and block 262, pump 20 is started and, as represented at line 264 and block 266, the controller 56 evokes a message to the operator at display 86 indicating that a purging operation is under way. The program then continues as represented at line 268 and block 270 to determine whether a requisite interval for purging has elapsed. In this regard, the user may find it valuable to assure that the purging operation is carded on for a minimum interval of time to assure clearance of the passageway. Accordingly, in the event the time-out is not concluded, then as represented at lines 272 and 264, the program dwells pending time-out for this function. Then, as represented at line 274 and block 276, following the interval of time-out, a second check is made to assure that the status of the liquid detector is one wherein no incursion condition exists. Upon acquiring the condition of detector 50, then as represented at line 278 and block 280, a test is made of the acquired information as to whether liquid is present at the detector 50. In the event that it is, then as represented at lines 282 and 274, the program loops until such time as the purge activity has cleared the passageways of incursive liquids and the like. Where no further liquid is present and the incursion output condition from detector 50 has ceased, then as represented at line 284 and block 286, the pump 20 is stopped in preparation for the reinstallation of the housing of water separator component 16. The program then continues as represented at line 288 and node B. Referring again to FIG. 3, node B is seen to reappear in conjunction with line 290 leading to line 186 wherein the program continues in general manner determining whether or not the separator component 16 has been installed.

Since certain changes may be made in the above-described apparatus without departing from the scope of the invention herein involved, it is intended that all matter contained in the description thereof or shown in the accompanying drawings shall be interpreted as illustrative and not in a limiting sense.

I claim:

1. In a gas analyzer assembly having a removable liquid extracting component with an extracting input and an extracting output, a gas analyzer having an analyzer input connected in gas transfer relationship with said extracting output and an analyzer output, and a pump actuable between off and on states and having a suction side connected in gas transfer relationship with said analyzer output, an output side and normally operative to establish a gas flow path from said extracting input through said analyzer output, the improvement comprising:
   a liquid detector having a detector input and a detector output and coupled in gas transfer relationship between said extracting output and said analyzer input and providing an incursion output condition in the presence of non-gaseous material therein;
   a flow control assembly having a primary inlet coupled with said detector output and a flow output coupled with said analyzer input and actuable between a flow state effecting the passage of a gas from said detector output into said analyzer input and a blocking state blocking the passage of said gas into said analyzer input; and
   interrupt control means responsive to said incursion output condition for actuating said flow control assembly to effect said blocking state, thereby interrupting said gas flow path and suspending the flow of gas therethrough.

2. The gas analyzer assembly of claim 1 in which said interrupt control means is responsive to said incursion output condition to actuate said pump into said off-state.

3. In a gas analyzer assembly having a liquid separator with a removable housing connected with said assembly, first and second chambers disposed within the housing, a wall formed of a gas permeable and liquid impermeable material separating said first from said second chamber, an input passage for introducing a gas sample containing a liquid into said first chamber with a first portion of the gas passing through said wall to the second chamber and a second portion of the gas and said liquid remaining in the first chamber, an output flow port for conveying the first portion of the gas from the second chamber, a receptacle mounted on the housing, a separator receptacle output connected in fluid flow communication with said first chamber and said receptacle, a gas analyzer component having an analyzer input connected in fluid transfer relationship with said output flow port and having an analyzer output, a pump having a suction side connected in gas transfer relationship with said analyzer output and having a pump output side, the improvement comprising:
   a first valve assembly having a primary inlet for receiving fluid flow from said output flow port, and a valve output coupled with said analyzer input, and actuable between a flow state effecting a passage of fluid to said analyzer input and a blocking state blocking said passage of fluid from said valve output into said analyzer input;
   passage means for conveying fluid from said output flow port to said first valve assembly primary inlet;
   a second valve assembly having a purge input coupled in gas transfer relationship with said pump output side, an expel output and a purge output and actuable between an expel state providing a fluid path between said purge input and said expel output and a purge state providing a fluid flow path between said purge input and said purge output;
   an interlock monitor operatively associated with said liquid separator having a connect output when said liquid separator housing is connected with said gas analyzer assembly and a disconnect output when said housing is removed from said analyzer assembly; and
   control means for selectively actuating said first valve assembly into said blocking state and said second valve assembly into said purge state when said interlock monitor disconnect output is present.

4. The improved assembly of claim 3 in which said first valve assembly is a three-way valve having a purge inlet connected in fluid flow transfer relationship with said second valve assembly purge output and providing a fluid flow path from said purge inlet to said primary inlet while blocking said valve output when in said blocking state.

5. The improved assembly of claim 3 including:
   a liquid detector having a detector input and a detector output coupled in fluid transfer relationship with said passage means and providing an incursion output condition in the presence of liquid therein; and
   said control means is responsive to said incursion output condition for actuating said first valve assembly into said blocking state.

6. The improved assembly of claim 5 including:
   display means responsive to a warning display signal to provide a visual prompt output representing advice for removing said liquid separator housing; and
   said control means is responsive to said incursion output condition for deriving said warning display signal.

7. In a gas analyzer assembly having a removable liquid extracting component with a component input and a component output, a gas analyzer having an analyzer input and an analyzer output, an intermediate passageway connected in fluid flow communication between said component output and said analyzer input, and a pump actuable between on and off states, having a suction side connected in fluid flow relationship with said analyzer output and an output side and normally operative to establish a forward gas flow path from said component input through said analyzer output, the improvement comprising:

an interlock monitor operatively associated with said liquid extracting component having a connect output when said liquid extracting component is operationally connected with said passageway and a disconnect output when said component is disconnected from said passageway; and control means responsive to said interlock monitor outputs for effecting termination of said forward gas flow in the presence of said disconnect output.

8. The improved assembly of claim 7 in which said control means is responsive to said interlock outputs in the presence of said disconnect output to actuate said pump to effect a reversal of said forward gas flow.

9. The improved assembly of claim 7 including:

a purge valve having a purge input coupled in gas transfer relationship with said pump output side, an expel output and a purge output and actuable between an expel state providing a fluid path between said purge input and said expel output, and a purge state providing a fluid flow path between said purge input and said purge output, thence to said intermediate passageway; and said control means is responsive to said interlock monitor outputs for effecting said actuation of said purge valve into said purge state only in the presence of said disconnect output.

10. The improved assembly of claim 9 in which said control means is responsive to said incursion output condition for actuating said pump into said off state and subsequently is responsive to said disconnect output when said purge valve is in said purge state for actuating said pump into said on state for at least a predetermined interval.

11. The improved assembly of claim 7 including:

a blocking valve assembly having a primary inlet coupled with said intermediate passageway and a valve output coupled in fluid flow communication with said analyzer input, and actuable between a flow state effecting a passage of fluid from said intermediate passageway to said analyzer input and a blocking state blocking said passage of fluid; and said control means is responsive to said disconnect output for actuating said blocking valve assembly into said blocking state.

12. The improved assembly of claim 11 including:

a liquid detector having a detector input and a detector output coupled in fluid flow communication with said intermediate passageway between said liquid extracting component and said blocking valve assembly and providing an incursion output condition in the presence of liquid therein; and said control means is responsive to said incursion output condition for actuating said blocking valve assembly into said blocking state.

13. The improved assembly of claim 12 including:

display means responsive to a warning display signal to provide a visual prompt output representing advice for an unacceptable status of said liquid extracting component; and said control means is responsive to said incursion output condition for deriving said warning display signal.

14. The improved assembly of claim 7 including a suction passageway in fluid flow communication between said pump suction side and atmospheric air in the presence of said disconnect output.

15. In a method of using a gas analyzer assembly having a removable liquid extracting component with an extractor input and an extractor output, a gas analyzer having an analyzer input connected in gas transfer relationship with said extractor output and an analyzer output, and a pump actuable between off and on states and having a suction side connected in gas transfer relationship with said analyzer output, an output side, and normally operative to establish a gas flow path extending in a forward direction from said extractor input through said analyzer output, the method for preventing the incursion of fluid into said gas analyzer comprising the steps of:

monitoring said extractor output to detect the presence of liquid moving therethrough;

providing an incursion signal upon said detection of liquid;

terminating the flow of gas in said forward direction along said gas flow path in the presence of said incursion signal;

monitoring the presence of said extracting component in an operative position within said gas analyzer assembly;

providing a disconnect output when said extracting component is removed from said operative position; and reversing the said forward direction of said gas flow path in the presence of said incursion signal in response to said disconnect output.

16. In a gas analyzer assembly having a removable liquid extracting component with an extracting input and an extracting output, a gas analyzer having an analyzer input connected in gas transfer relationship with said extracting output and an analyzer output, and a pump actuable between off and on states and having a suction side connected in gas transfer relationship with said analyzer output, an output side and normally operative to establish a gas flow path from said extracting input through said analyzer output, the improvement comprising:

a liquid detector having a detector input and a detector output and coupled in gas transfer relationship between said extracting output and said analyzer input and providing an incursion output condition in the presence of non-gaseous material therein;

display means responsive to a warning display signal to provide a visual prompt output representing a failure of said liquid extracting component; and interrupt control means responsive to said incursion output condition for interrupting said gas flow path and suspending a flow of gas therethrough and for deriving said warning display signal.

17. In a gas analyzer assembly having a removable liquid extracting component with an extracting input and an extracting output, a gas analyzer having an analyzer input connected in gas transfer relationship with said extracting output and an analyzer output, and a pump actuable between off and on states and having a suction side connected in gas transfer relationship with said analyzer output, an output side and normally operative to establish a gas flow path from said extracting input through said analyzer output, the improvement comprising:

a liquid detector having a detector input and a detector output and coupled in gas transfer relationship between said extracting output and said analyzer input and providing an incursion output condition in the presence of non-gaseous material therein;

an interlock monitor, operatively associated with said liquid extracting component, having a connect output when said liquid extracting component is connected with said gas analyzer assembly and a disconnect output when said liquid extracting component is removed from said analyzer assembly; and interrupt control means responsive to said incursion output condition for interrupting said gas flow path and suspending a flow of gas therethrough and being further responsive to said disconnect output in the presence of said incursion output condition and a subsequent said connect output in the absence of said incursion output condition to reinstate said gas flow path from said extracting input through said analyzer output.

18. In a gas analyzer assembly having a removable liquid extracting component with an extracting input and an extracting output, a gas analyzer having an analyzer input connected in gas transfer relationship with said extracting output and an analyzer output, and a pump actuable between off and on states and having a suction side connected in gas transfer relationship with said analyzer output, an output side and normally operative to establish a gas flow path from said extracting input through said analyzer output, the improvement comprising:

a liquid detector having a detector input and a detector output and coupled in gas transfer relationship between said extracting output and said analyzer input and providing an incursion output condition in the presence of non-gaseous material therein;

a flow control assembly having a primary inlet coupled with said detector output and a flow output coupled with said analyzer input and actuable between a flow state effecting the passage of a gas from said detector output into said analyzer input and a blocking state blocking the passage of said gas into said analyzer input;

alarm means energizable to provide an audibly perceptible output; and interrupt control means responsive to said incursion output condition for interrupting said gas flow path and suspending a flow of gas therethrough, for energizing said alarm means, and being further responsive to said incursion output condition to actuate said flow control assembly into said blocking state.

19. In a gas analyzer assembly having a removable liquid extracting component including a removable liquid receptacle with an extracting input and an extracting output including a first output and a second output coupled in fluid flow relationship with said receptacle, a gas analyzer having an analyzer input connected in gas transfer relationship with said extracting output and an analyzer output, and a pump actuable between off and on states and having a suction side connected in gas transfer relationship with said analyzer output, an output side and normally operative to establish a gas flow path from said extracting input through said analyzer output, the improvement comprising:

a liquid detector having a detector input connectable in fluid flow relationship with said first output and a detector output and coupled in gas transfer relationship between said extracting output and said analyzer input and providing an incursion output condition in the presence of non-gaseous material therein;

a flow control assembly having a primary inlet coupled with said detector output and a flow output coupled with said analyzer input and actuable between a flow state effecting the passage of a gas from said detector output into said analyzer input and a blocking state blocking the passage of said gas into said analyzer input, said flow control assembly including a purge inlet configured for providing a gas flow path from said purge inlet into said primary inlet when in said blocking state;

suction conduit means for providing a fluid flow relationship between said pump suction side and said second output and communicating with atmospheric air in the absence of said liquid receptacle;

a purge valve having a purge input coupled in gas transfer relationship with said pump output side, a purge expel output and a purge output and actuable between an expel state providing a fluid flow path between said purge input and said purge expel output and a purge state providing a fluid flow path between said purge input and said purge output;

purge conduit means for providing fluid flow transfer from said purge output to said flow control assembly purge inlet when said flow control assembly is in said blocking state and said purge valve is in said purge state;

said flow control assembly including a purge inlet configured for providing a gas flow path from said purge inlet into said primary inlet when in said blocking state; and interrupt control means responsive to said incursion output condition for interrupting said gas flow path and suspending a flow of gas therethrough, and being further responsive to said incursion output condition to actuate said flow control assembly into said blocking state.

20. The gas analyzer assembly of claim 19 in which said interrupt control means is responsive to said incursion output condition for actuating said purge valve into said purge state.

21. The gas analyzer assembly claim 29 including:
display means responsive to a warning display signal to provide a visual prompt output representing advice for removing said liquid extracting component;

an interlock monitor operatively associated with said liquid extracting component having a connect output when said liquid extracting component is connected with said gas analyzer assembly and a disconnect output when said liquid extracting component is removed from said analyzer assembly; and said interrupt control means is responsive to said incursion output condition for providing said warning display signal, and is subsequently responsive to said disconnect output for actuating said purge valve into said purge state.

22. The gas analyzer assembly of claim 19 including:
display means responsive to a warning display signal to provide a visual prompt output representing advice for removing said liquid extracting component;

an interlock monitor operatively associated with said liquid extracting component having a connect output when said liquid extracting component is connected with said gas analyzer assembly and a disconnect output when said liquid extracting component is removed from said gas analyzer assembly; and said interrupt control means is responsive to said incursion output condition in the presence of said connect output for providing said warning display signal and for actuating said pump into said off state, and is responsive to said disconnect output in the presence of said incursion output condition for actuating said purge valve into said purge state and for actuating said pump into said on state.

23. The gas analyzer assembly of claim 22 in which said interrupt control means is responsive to said disconnect output in the presence of said incursion output condition for actuating said pump into said on state for at least a predetermined interval of time.

* * * * *